(12) United States Patent
Doi et al.

(10) Patent No.: US 9,999,358 B2
(45) Date of Patent: Jun. 19, 2018

(54) BLOOD PRESSURE MEASUREMENT DEVICE

(71) Applicant: OMRON HEALTHCARE CO., LTD., Muko-shi, Kyoto (JP)

(72) Inventors: Ryosuke Doi, Kyoto (JP); Shingo Yamashita, Kyoto (JP); Masataka Yanagase, Kyoto (JP); Yukiya Sawanoi, Kyoto (JP); Chisato Uesaka, Kyoto (JP); Naoki Miyakawa, Kyoto (JP); Hiroshi Koshimizu, Kyoto (JP); Kenichiro Zaitsu, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 825 days.

(21) Appl. No.: 14/456,629

(22) Filed: Aug. 11, 2014

(65) Prior Publication Data
US 2014/0350419 A1    Nov. 27, 2014

Related U.S. Application Data

(63) Continuation of application No. PCT/JP2012/079277, filed on Nov. 12, 2012.

(30) Foreign Application Priority Data

Mar. 19, 2012 (JP) ................. 2012-061929

(51) Int. Cl.
*A61B 5/00* (2006.01)
*A61B 5/022* (2006.01)

(52) U.S. Cl.
CPC .. *A61B 5/02233* (2013.01); *A61B 2560/0276* (2013.01)

(58) Field of Classification Search
None
See application file for complete search history.

(56) References Cited

U.S. PATENT DOCUMENTS 4,353,374 A * 10/1982 Rebbe ............... A61B 5/02233
                                                        600/499
2006/0005361 A1 * 1/2006 O'Banion ............... A42B 1/24
                                                        24/303

(Continued)

FOREIGN PATENT DOCUMENTS

CN    102307519 A    1/2012
JP    U-62-61204    4/1987

(Continued)

OTHER PUBLICATIONS

International Search Report issued in PCT/JP2012/079277 dated Dec. 4, 2012.

(Continued)

*Primary Examiner* — Tiffany Weston
*Assistant Examiner* — Sarah Kingsley
(74) *Attorney, Agent, or Firm* — Oliff PLC

(57) ABSTRACT

A blood pressure measurement device includes a cuff and a control unit. The cuff includes a first securing portion, provided on one surface of the cuff, for securing the cuff to the measurement area in a wrapped state, and a second securing portion, provided on another surface of the cuff, for securing the cuff to the measurement area in a wrapped state. At least one of the first securing portion and the second securing portion includes an electromagnet portion. The control unit secures the cuff to the measurement area by controlling a magnetic force emitted from the electromagnet portion and causing the second securing portion to be attracted to the first securing portion.

13 Claims, 10 Drawing Sheets

(56) References Cited

U.S. PATENT DOCUMENTS

2011/0112412 A1* 5/2011 Sano ................. A61B 5/02141
　　　　　　　　　　　　　　　　　　　　　　　　600/499
2011/0225697 A1* 9/2011 Griffits ................ H04N 5/4403
　　　　　　　　　　　　　　　　　　　　　　　　2/69

FOREIGN PATENT DOCUMENTS

| JP | U-3076809 | 4/2001 | |
| JP | 2006-102188 A | 4/2006 | |
| JP | WO 2010004840 A1 * | 1/2010 | ......... A61B 5/02141 |
| JP | A-2010-130244 | 6/2010 | |
| WO | WO 2010/089917 A1 | 8/2010 | |

OTHER PUBLICATIONS

Jun. 30, 2015 Chinese Office Action issued in Chinese Patent Application No. 201280070283.6.

* cited by examiner

BLOOD PRESSURE MEASUREMENT DEVICE

This is a Continuation of International Application No. PCT/JP2012/079277 filed Nov. 12, 2012, which claims the benefit of Japanese Application No. 2012-061929 filed Mar. 19, 2012. The disclosure of the prior applications is hereby incorporated by reference herein in its entirety.

TECHNICAL FIELD

The present invention relates to blood pressure measurement devices.

BACKGROUND ART

A blood pressure measurement device that employs a cuff containing an air bladder for pressurizing an artery located in an arm of a measurement subject has been proposed. To measure a blood pressure value using such a blood pressure measurement device, the cuff is wrapped tightly around the arm and the wrapped cuff is then secured in place.

After the cuff has been secured in place, air is injected into the air bladder of the cuff, and arterial pulse waves occurring in the artery are detected by pressurizing and depressurizing the arm. The blood pressure is measured in this manner.

Patent Literature 1 discloses a configuration in which the cuff is positioned on the arm using a magnet, a magnetic body, or the like, and a surface fastener is employed to secure the cuff in place.

CITATION LIST

Patent Literature

Patent Literature 1: JP-62-61204U

SUMMARY OF INVENTION

Technical Problem

In the case where a surface fastener is employed to secure the cuff in place, as with Patent Literature 1, a set amount of force is required to remove the attached surface fastener when removing the cuff from the arm after the blood pressure measurement is complete. It can thus be difficult for measurement subjects who lack such strength, such as the elderly, women, and so on, to remove the cuff.

In addition, the surface fastener produces noise when the cuff is removed from the arm. Such noise can be bothersome for measurement subjects. Such noise can also make it difficult to comfortably use such a blood pressure measurement device in places where it is necessary to be considerate of other people aside from the measurement subject.

Furthermore, repeated use of the surface fastener causes the surface fastener material to degrade, which leads to a drop in the strength with which the surface fastener can secure the cuff. As a result, the cuff can come loose during inflation, making it impossible to carry out the measurement.

Further still, when securing a cuff using a surface fastener, it is necessary to provide a wide surface area for the surface fastener. This reduces the freedom with which the blood pressure measurement device can be designed.

Having been achieved to solve the aforementioned problems, it is an object of the present invention to provide a novel blood pressure measurement device that does not employ a surface fastener to secure a cuff.

Solution to Problem

A blood pressure measurement device according to an aspect of the invention includes a cuff that is used by being wrapped around a measurement area. The cuff includes a first securing portion, provided on one surface of the cuff, for securing the cuff to the measurement area in a wrapped state, and a second securing portion, provided on another surface of the cuff, for securing the cuff to the measurement area in a wrapped state. At least one of the first securing portion and the second securing portion includes an electromagnet portion. The blood pressure measurement device further includes a control unit that secures the cuff to the measurement area by controlling a magnetic force emitted from the electromagnet portion and causing the second securing portion to be attracted to the first securing portion.

Advantageous Effects of Invention

According to the stated blood pressure measurement device, the cuff is secured using the magnetic force emitted from the electromagnet portion. Accordingly, the strength at which the cuff is secured can be varied in accordance with the magnitude of the magnetic force emitted from the electromagnet portion. This makes it easy to remove the cuff. Furthermore, no noise is produced when the cuff is removed from the arm. Further still, there is no material degradation as with a surface fastener, which makes it possible to continue to use the blood pressure measurement device for long periods of time. In addition, the magnetic force emitted from the electromagnet portion varies depending on the magnitude of a current that is flowing and the like, and thus a large surface area does not need to be ensured for the electromagnet portion in order to ensure that the cuff is strongly secured.

DESCRIPTION OF EMBODIMENTS

Hereinafter, an embodiment of the present invention will be described with reference to the drawings.

Figure 1:
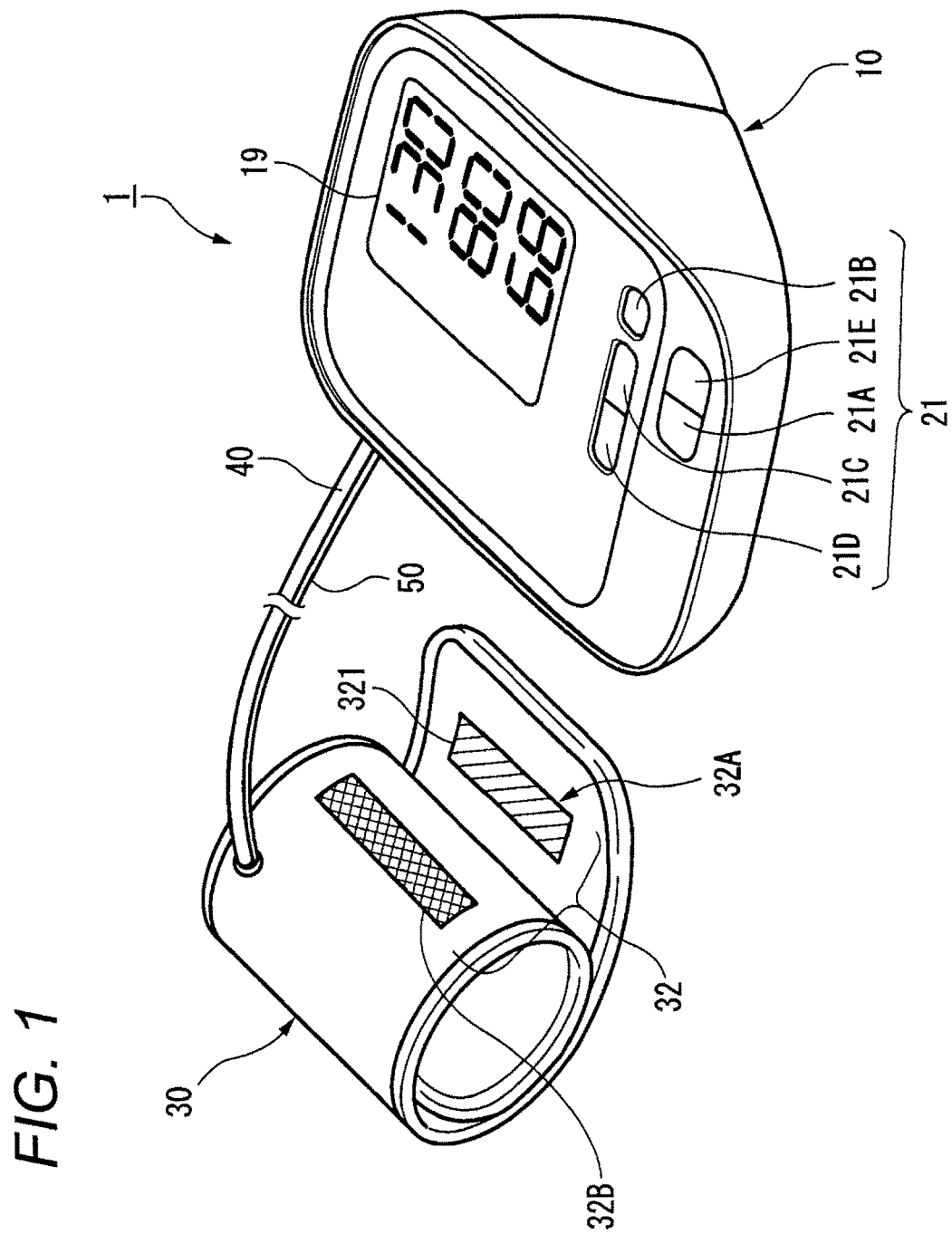
FIG. 1 is an external view of the overall configuration of a blood pressure measurement device, illustrating an embodiment of the present invention.

FIG. 1 is an external view of the overall configuration of a blood pressure measurement device 1, illustrating an embodiment of the present invention.

The blood pressure measurement device 1 includes a main body unit 10, a cuff 30 that can be wrapped around a measurement subject's upper arm, and an air tube 40 and a power supply line 50 that connect the main body unit 10 to the cuff 30.

As described in the present specification, "cuff" refers to a band-shaped or cylindrical structure, having an interior space, that can be wrapped around a measurement area of a body (an upper arm, a wrist, or the like), and that is used to measure a blood pressure by pressurizing the measurement subject's artery when a fluid such as a gas, a liquid, or the like is injected into the interior space.

"Cuff" is a term indicating a concept that includes a fluid bladder and a wrapping means for wrapping the fluid bladder around the body, and is also sometimes referred to as a "manchette".

The main body unit 10 includes a display unit 19, configured of a liquid-crystal panel, for example, for displaying various types of information such as blood pressure values, pulse frequencies, and the like, as well as an operating unit 21 for accepting instructions from a user (the measurement subject).

The operating unit 21 includes a power switch 21A for accepting the input of an instruction for turning the power on or off, a memory switch 21B for accepting instructions for reading out information such as blood pressure data and the like stored in the main body unit 10 and displaying the read-out information in the display unit 19, arrow switches 21C and 21D for accepting instructions for incrementing/decrementing memory numbers when calling information, and a measure/stop switch 21E for accepting instructions for starting and stopping measurement.

Figure 2:
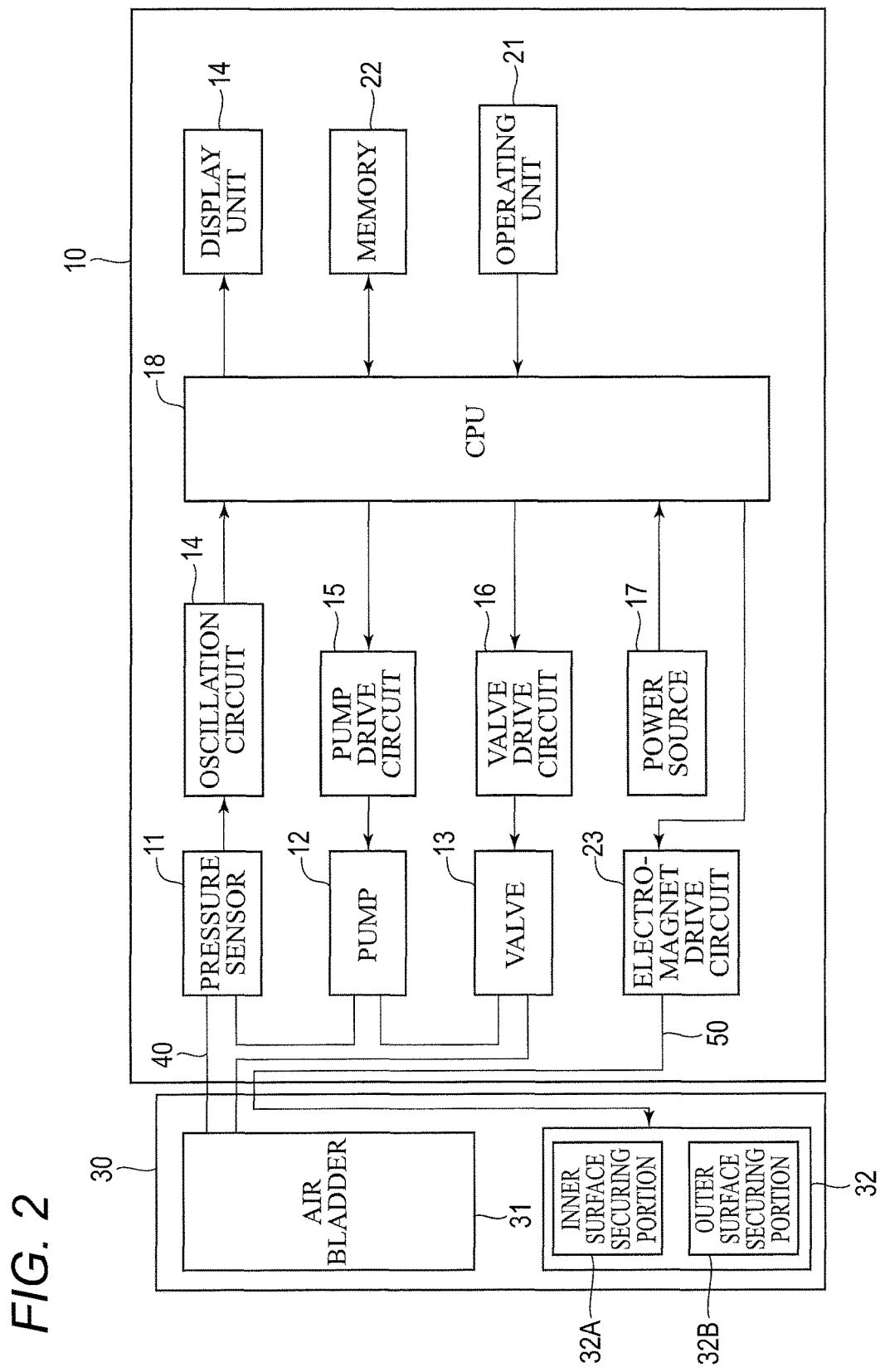
FIG. 2 is a diagram illustrating the internal configuration of the blood pressure measurement device illustrated in FIG. 1.

FIG. 2 is a diagram illustrating the internal configuration of the blood pressure measurement device 1 shown in FIG. 1.

The cuff 30 contains an air bladder 31 serving as the aforementioned fluid bladder, and the air tube 40 shown in FIG. 1 is connected to this air bladder 31.

The cuff 30 also includes a securing portion 32 for securing the cuff 30 to the measurement area, and the power supply line 50 shown in FIG. 1 is connected to the securing portion 32.

The main body unit 10 includes a pressure sensor 11, a pump 12, and an exhaust valve (called simply a "valve" hereinafter) 13 that are connected to the air tube 40, an oscillation circuit 14, a pump drive circuit 15, a valve drive circuit 16, a power source 17 that supplies power to the various units in the main body unit 10, the display unit 19 illustrated in FIG. 1, a control unit (CPU) 18 that carries out various types of computational processes for controlling the main body unit 10 as a whole, the operating unit 21 shown in FIG. 1, a memory 22, and a electromagnet drive circuit 23 connected to the power supply line 50.

The pump 12 supplies air to the air bladder 31 in order to increase the pressure with which the cuff 30 pressurizes the measurement area.

The valve 13 is opened/closed in order to exhaust or inject air from or into the air bladder 31.

The pump drive circuit 15 controls the driving of the pump 12 based on a control signal supplied from the CPU 18.

The valve drive circuit 16 controls the opening/closing of the valve 13 based on a control signal supplied from the CPU 18.

The pump 12, the valve 13, the pump drive circuit 15, and the valve drive circuit 16 configure a pressurizing pressure adjustment unit that varies the pressure with which the cuff 30 pressurizes the measurement area.

An electrostatic capacitance pressure sensor, for example, is used for the pressure sensor 11. With an electrostatic capacitance pressure sensor, a capacity value changes in accordance with a detected pressure.

The oscillation circuit 14 oscillates based on a capacity value of the pressure sensor 11 and outputs signal in accordance with that capacity value to the CPU 18. The CPU 18 detects the pressure in the cuff 30 (a cuff pressure) by converting the signal outputted from the oscillation circuit 14 into a pressure value.

The memory 22 includes a read-only memory (ROM) that stores programs, data, and so on for causing the CPU 18 to perform predetermined operations, a random access memory (RAM) used as a working area, and a flash memory that holds measured blood pressure data and the like.

The electromagnet drive circuit 23 drives an electromagnet portion 321, provided in the securing portion 32 and mentioned later, based on a control signal supplied from the CPU 18. In other words, the electromagnet drive circuit 23 supplies a predetermined power to the securing portion 32 based on a control signal from the CPU 18.

As shown in FIGS. 1 and 2, the securing portion 32 includes an inner surface securing portion 32A, provided on an inner surface of the cuff 30 and that secures the cuff 30 while the cuff 30 is wrapped around the measurement area, and an outer surface securing portion 32B, provided on an outer surface of the cuff 30 and that secures the cuff 30 while the cuff 30 is wrapped around the measurement area.

The inner surface securing portion 32A includes the electromagnet portion 321, which attracts and secures the outer surface securing portion 32B. The electromagnet portion 321 produces a magnetic force based on power supplied from the electromagnet drive circuit 23 via the power supply line 50.

On the other hand, the outer surface securing portion 32B does not include an electromagnet, and is instead formed of a magnetic body.

When power is supplied to the electromagnet portion 321, the inner surface securing portion 32A attracts and secures the outer surface securing portion 32B due to the magnetic force produced by the electromagnet portion 321. The cuff 30 is secured to the measurement area as a result.

Although the electromagnet portion is provided in the inner surface securing portion 32A in the blood pressure measurement device 1, it should be noted that the electromagnet portion may be provided in the outer surface securing portion 32B and the inner surface securing portion 32A may be configured of a magnetic body.

In this case, the electromagnet drive circuit 23 supplies the power to the electromagnet in the outer surface securing portion 32B.

Figure 3:
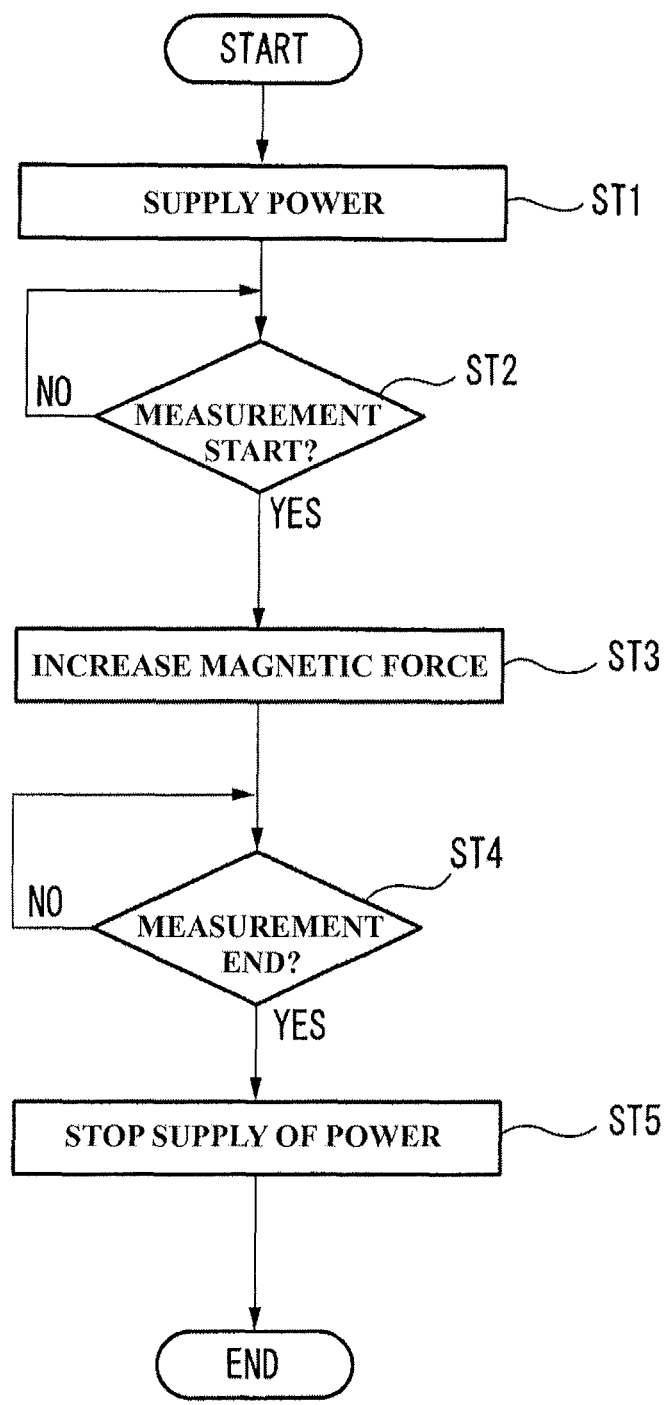
FIG. 3 is a flowchart illustrating control of an electromagnet portion performed when measuring a blood pressure using the blood pressure measurement device shown in FIG. 1.

FIG. 3 is a flowchart illustrating control of the electromagnet portion performed when measuring a blood pressure using the blood pressure measurement device shown in FIG. 1.

First, in response to the power switch 21A being pressed, the CPU 18 causes power to be supplied to the electromagnet portion 321 from the electromagnet drive circuit 23 (ST1).

Next, the CPU 18 maintains the supply of power to the electromagnet portion 321 so that the magnetic force emitted from the electromagnet portion 321 remains constant, without changing, until the measure/stop switch 21E is pressed (ST2—NO).

When the measure/stop switch 21E has been pressed (ST2—YES), the CPU 18 drives the pump 12, supplying air to the air bladder 31 in the cuff 30, and increases the magnetic force emitted from the electromagnet portion 321 in accordance with the pressurizing pressure in the cuff 30 (ST3).

The CPU 18 increases the magnetic force by, for example, increasing a current that flows in the electromagnet portion 321.

Through this, the inner surface securing portion 32A more strongly attracts the outer surface securing portion 32B, thus securing the outer surface securing portion 32B more strongly. In other words, the cuff 30 is more strongly secured.

As opposed to this, in the case where a surface fastener is employed to secure the cuff, the surface fastener can shift while the cuff 30 is being inflated, and the amount of air required to measure the blood pressure can increase as a result.

Accordingly, there are cases where the blood pressure measurement device consumes a greater amount of power, increased performance is required of the pump in order to supply the air to the air bladder, and so on. Furthermore, vibrations resulting from the surface fastener shifting can produce noise, which can affect the accuracy of the blood pressure measurement. However, using the electromagnet portion 321 as described above can reduce the occurrence of such shifting.

When, after the blood pressure measurement has been started, the CPU 18 determines that the pressure value has reached a predetermined level based on a signal outputted from the pressure sensor 11 in response to the rise in the cuff pressure, the CPU 18 gradually opens the valve 13 that had been closed, carrying out slow exhaust control and gradually reducing the cuff pressure. As the cuff pressure decreases, the CPU 18 calculates blood pressure values (a systolic blood pressure and a diastolic blood pressure) according to a predetermined procedure, based on a pulse pressure signal that is superimposed on the signal detected by the pressure sensor 11. This blood pressure calculation procedure is a known technique, and thus descriptions thereof will be omitted here.

The CPU 18 carries out control so that power is supplied to the electromagnet portion 321 so that the magnetic force emitted by the electromagnet portion 321 remains high until the blood pressure values are calculated (ST4).

Once the CPU 18 has calculated the blood pressure value, the blood pressure measurement ends (ST4—YES), and the blood pressure values that have been obtained are displayed in the display unit 19.

After the obtained blood pressure values have been displayed in the display unit 19, the CPU 18 opens the valve 13 completely and vents the air from the air bladder 31 in the cuff 30.

Furthermore, in accordance with the end of the blood pressure measurement, the CPU 18 stops the supply of power to the electromagnet portion 321 (ST5).

As a result, a magnetic force is no longer emitted from the electromagnet portion 321, and the inner surface securing portion 32A and the outer surface securing portion 32B cease to attract each other. In other words, the cuff 30 ceases to be secured.

According to the blood pressure measurement device 1 as described thus far, the cuff 30 is secured using the magnetic force emitted from the electromagnet portion 321. Accordingly, the strength at which the cuff 30 is secured can be varied in accordance with the magnetic force emitted from the electromagnet portion 321, making it easy to remove the cuff 30.

Furthermore, no noise is produced when the cuff is removed from the arm.

Further still, there is no material degradation as with a surface fastener, which makes it possible to continue to use the blood pressure measurement device for long periods of time. Further still, the magnetic force emitted from the electromagnet portion 321 varies depending on the magnitude of a current that is flowing and the like, and thus the electromagnet portion 321 does not necessarily need to have a large surface area.

For this reason, using the electromagnet portion 321 increases the freedom of design.

Although the power switch 21A and the measure/stop switch 21E are provided in the operating unit 21 as separate switches in the blood pressure measurement device 1, the power switch may also function as the measure/stop switch.

In this case, when the power switch is pressed once, the CPU 18 may carry out control so that power is supplied to the electromagnet portion 321, and when the power switch is then pressed again, the magnetic force emitted from the electromagnet portion 321 may be increased.

Figure 4:
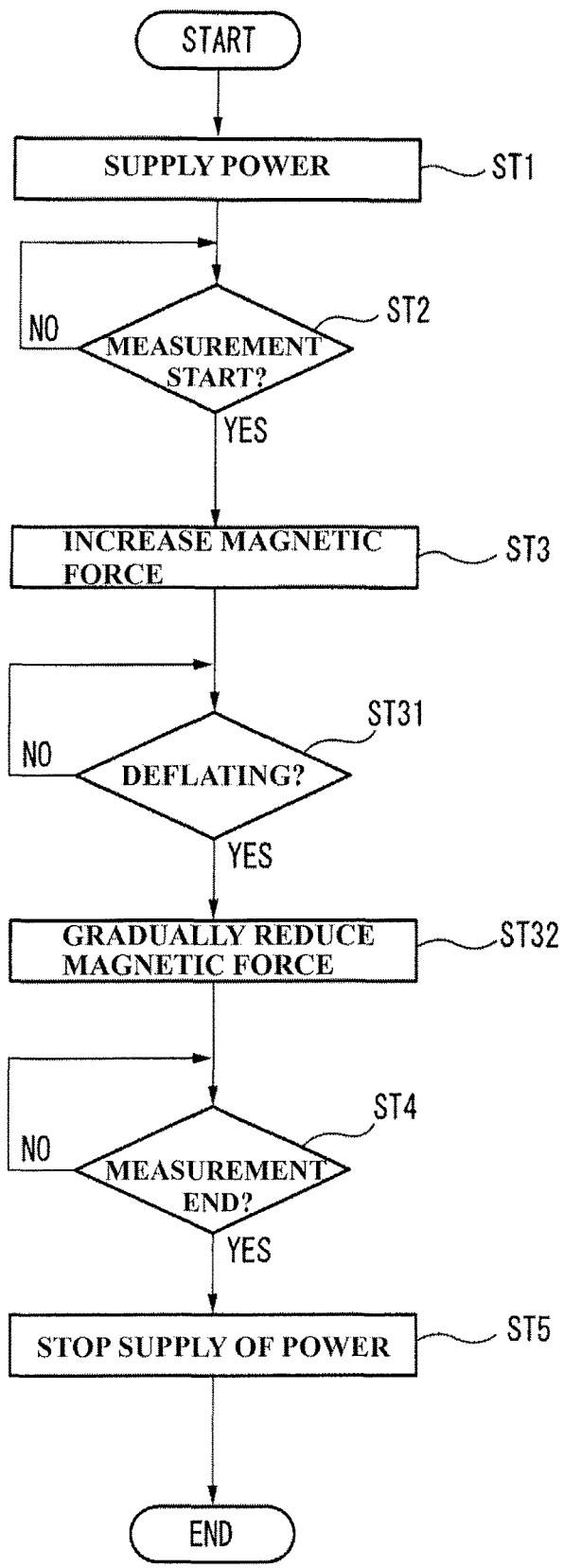
FIG. 4 is a flowchart illustrating another example of control of an electromagnet portion performed when measuring a blood pressure.

FIG. 4 is a flowchart illustrating another example of control of the electromagnet portion 321 performed when measuring a blood pressure.

The flowchart shown in FIG. 4 differs from the flowchart shown in FIG. 3 in that the control of the electromagnet portion 321 during blood pressure measurement has been changed.

Note that in FIG. 4, processes that are the same as those in FIG. 3 have been given the same reference numerals, and descriptions thereof will be omitted as appropriate.

According to the flowchart shown in FIG. 4, the CPU 18 carries out control so that the magnetic force emitted from the electromagnet portion 321 does not change until the deflation process for the blood pressure measurement has started.

Once the deflation process for the blood pressure measurement has started (ST31—Y), the magnetic force emitted from the electromagnet portion 321 is gradually reduced while the cuff 30 deflates (ST31—N).

The CPU 18 reduces the magnetic force by, for example, reducing the current that flows in the electromagnet portion 321.

By reducing the magnetic force emitted from the electromagnet portion 321 in accordance with the pressure in the cuff, the amount of power consumed by the blood pressure measurement device 1 can be reduced.

Figure 5:
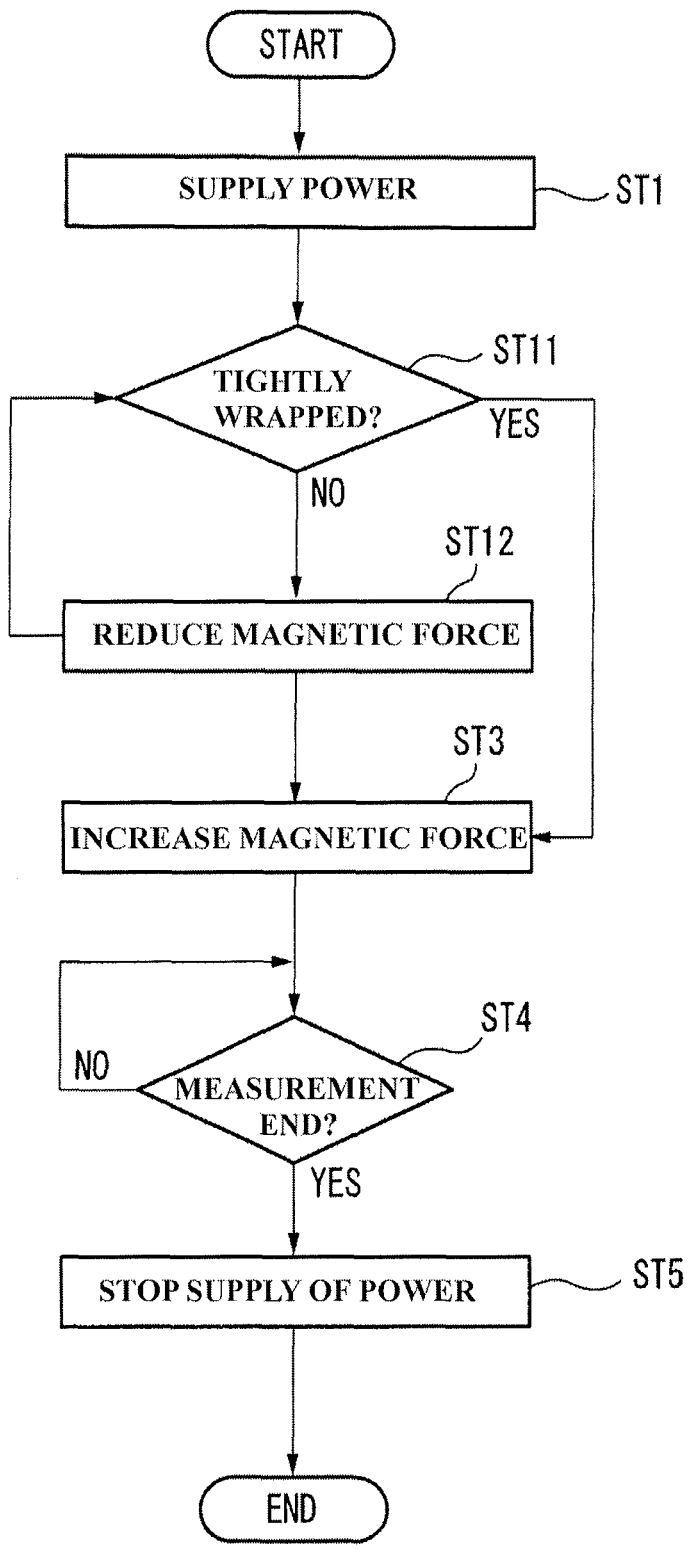
FIG. 5 is a flowchart illustrating yet another example of control of an electromagnet portion performed when measuring a blood pressure.

FIG. 5 is a flowchart illustrating yet another example of control of the electromagnet portion performed when measuring the blood pressure.

The flowchart shown in FIG. 5 differs from the flowchart shown in FIG. 3 in that after the power switch 21A has been pressed, the CPU 18 determines whether the cuff 30 is wrapped tightly around the measurement area and then carries out control that varies the magnetic force emitted from the electromagnet portion 321.

Note that in FIG. 5, processes that are the same as those in FIG. 3 have been given the same reference numerals, and descriptions thereof will be omitted.

Determining whether the cuff 30 is wrapped tightly (a wrapping state determination) is carried out as follows.

First, when the measure/stop switch 21E has been pressed, the CPU 18 causes a small amount of air to be supplied to the air bladder 31, thus performing a preparatory inflation of the cuff 30. A pressure value detected from the preparatory inflation is a value that is low but that enables the wrapping state to be determined. After the preparatory inflation, the CPU 18 uses the pressure sensor 11 to continuously measure the cuff pressure for a predetermined short interval of time (5.12 msec, for example).

An amount of change in the pressure value obtained through the measurement taken over this interval of time is then compared to a predetermined threshold. The CPU 18 determines that the cuff 30 is wrapped tightly when the amount of change is less than the predetermined threshold, and determines that the cuff 30 is not wrapped tightly when the amount of change is greater than or equal to the predetermined threshold.

When the CPU 18 has determined that the cuff 30 is wrapped tightly (ST11—Y), the process moves to the actual inflation, where the magnetic force emitted from the electromagnet portion 321 is increased in accordance with the pressurizing pressure in the cuff 30 (ST3) and the blood pressure measurement process is continued.

On the other hand, when the CPU 18 has determined that the cuff 30 is not tightly wrapped (ST11—N), the magnetic force emitted from the electromagnet portion 321 is reduced (ST12).

At this time, the CPU 18 displays a message reading "the cuff 30 is not tightly wrapped" in the display unit 19 so as to notify the measurement subject, and then causes the valve drive circuit 16 to completely open the valve 13 in order to vent the air bladder 31 in the cuff 30 and reset the state of the air bladder 31.

Upon receiving the notification, the measurement subject can adjust how the cuff is secured. The CPU 18 then determines whether the cuff 30 is tightly wrapped again after a predetermined amount of time has elapsed (ST11).

In this manner, when the cuff 30 is not tightly wrapped, the CPU 18 reduces the magnetic force emitted from the electromagnet portion 321. Accordingly, the force at which the inner surface securing portion 32A attracts the outer surface securing portion 32B weakens.

As a result, the measurement subject can easily adjust the position of the inner surface securing portion 32A relative to the outer surface securing portion 32B. In other words, it is easy to adjust how the cuff is secured.

The determination as to whether the cuff 30 is tightly wrapped is disclosed in detail in JP 2005-305028A, the content of which is incorporated herein by reference.

Figure 6:
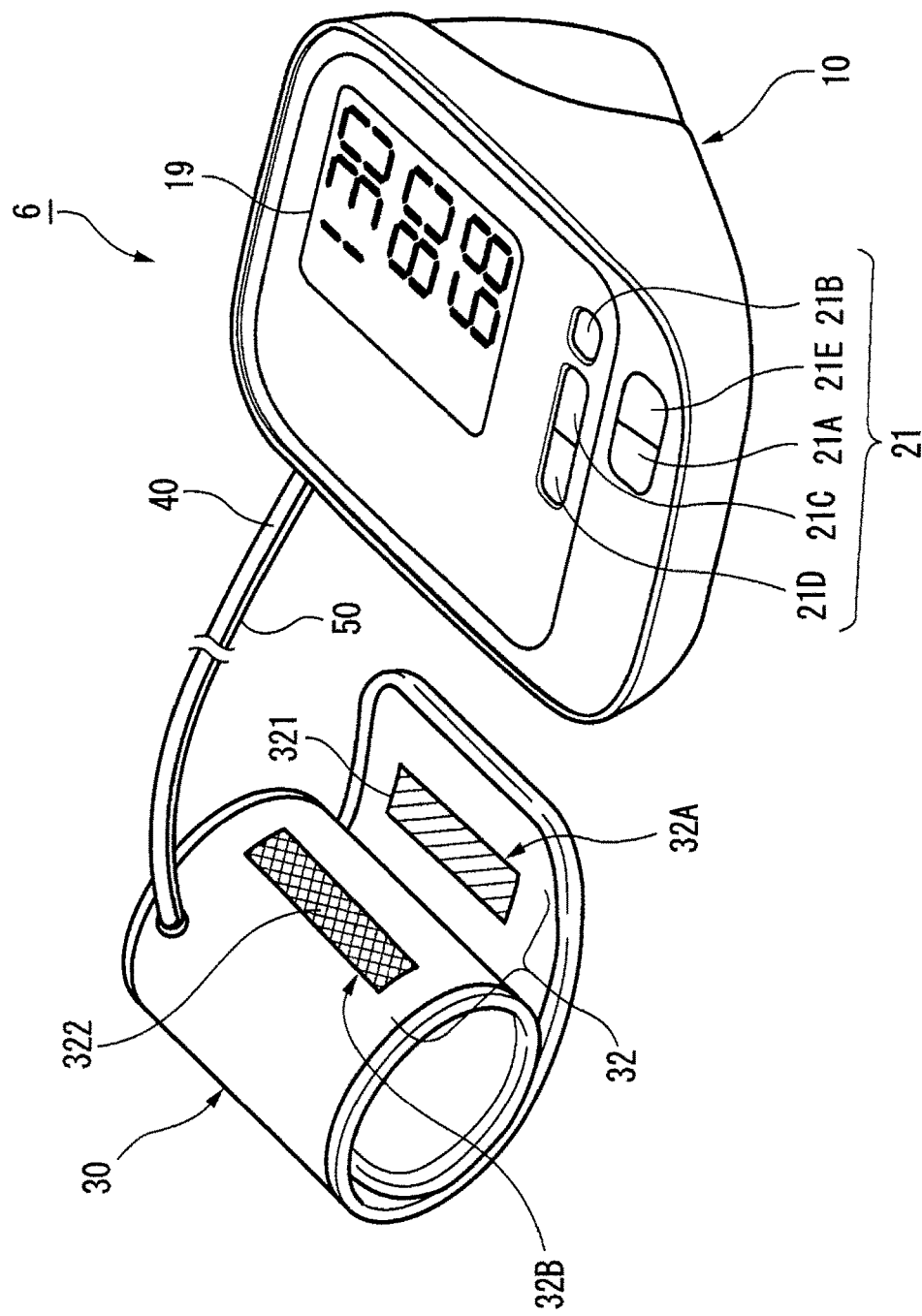
FIG. 6 is an external view illustrating another example of the blood pressure measurement device illustrated in FIG. 1.

FIG. 6 is an external view illustrating another example of the blood pressure measurement device 1.

As shown in FIG. 6, a blood pressure measurement device 6 differs from the blood pressure measurement device 1 in that the outer surface securing portion 32B also includes an electromagnet portion 322 that attracts and secures the inner surface securing portion 32A.

Note that in FIG. 6, constituent elements that are the same as those in FIG. 1 have been given the same reference numerals, and descriptions thereof will be omitted as appropriate.

In the blood pressure measurement device 6, the CPU 18 adjusts the magnetic force of the electromagnet portion 321 and the electromagnet portion 322. Specifically, the CPU 18 carries out control so that the magnetic force emitted from the electromagnet portion 321 and the electromagnet portion 322 have respectively opposite polarities (first control). Through this, the cuff 30 is secured as a result of the electromagnet portion 321 and the electromagnet portion 322 being attracted to each other.

Figure 7:
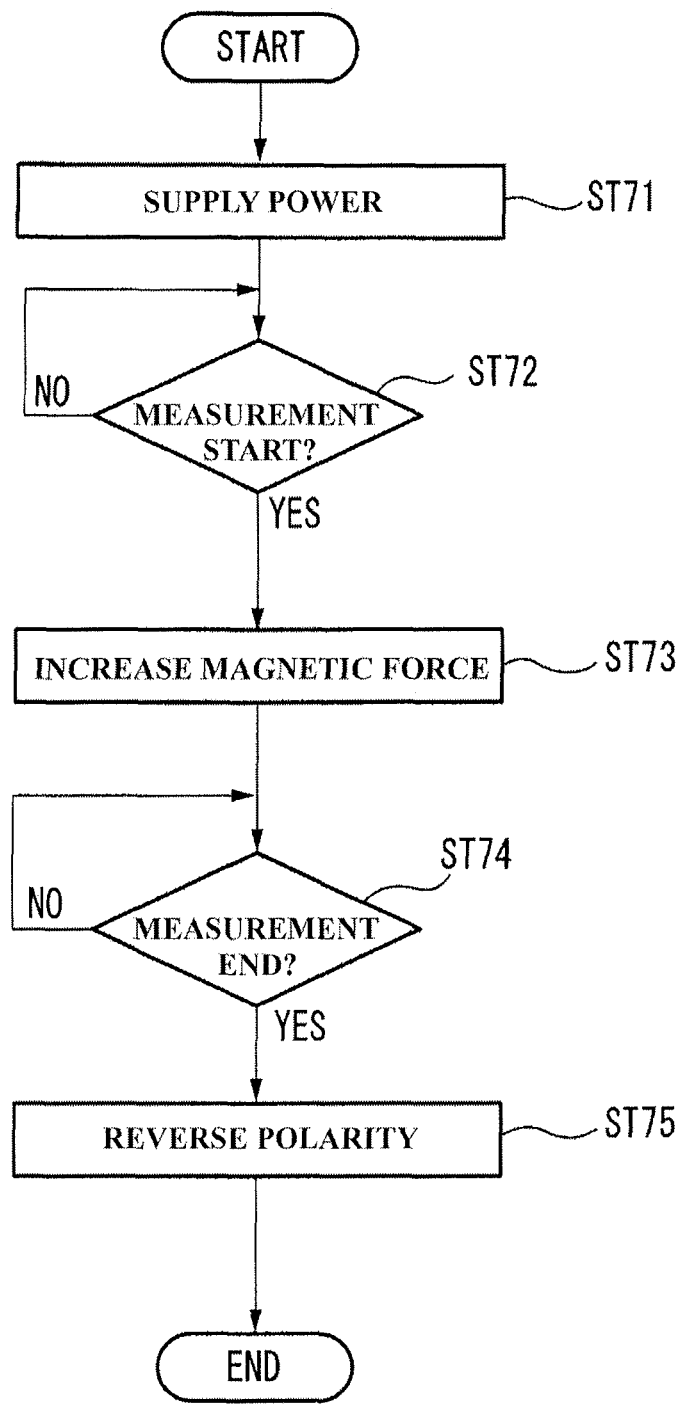
FIG. 7 is a flowchart illustrating control of an electromagnet portion performed when measuring a blood pressure using the blood pressure measurement device shown in FIG. 6.

FIG. 7 is a flowchart illustrating control of the electromagnet portion 321 and the electromagnet portion 322 performed when measuring a blood pressure using the blood pressure measurement device 6 shown in FIG. 6.

First, when the power switch 21A is pressed, the CPU 18 controls the electromagnet drive circuit 23 to supply power to the electromagnet portion 321, and furthermore controls the electromagnet drive circuit 23 to supply power to the electromagnet portion 322 as well (ST71).

Next, the CPU 18 maintains the supply of power to the electromagnet portion 321 and the electromagnet portion 322 so that the magnetic force emitted from the electromagnet portions remains constant, until the measure/stop switch 21E is pressed (ST72—NO).

When the measure/stop switch 21E has been pressed (ST72—YES), the CPU 18 drives the pump 12, supplying air to the air bladder 31 in the cuff 30, and increases the magnetic force emitted from the electromagnet portion 321 and the electromagnet portion 322 (ST73).

Note that the CPU 18 may instead increase the magnetic force emitted from only one of the electromagnet portion 321 and the electromagnet portion 322.

As in the flowchart shown in FIG. 3, the CPU 18 carries out control so that power is supplied to the electromagnet portion 321 and the electromagnet portion 322 so that the magnetic force emitted by the electromagnet portion 321 and the electromagnet portion 322 remains high until the blood pressure values are calculated (ST74).

Once the CPU 18 has calculated the blood pressure value as described above, the blood pressure measurement ends (ST74—YES), and the blood pressure values that have been obtained are displayed in the display unit 19.

After the obtained blood pressure values have been displayed in the display unit 19, the CPU 18 controls the valve 13 to open completely and vents the air from the air bladder 31 in the cuff 30.

Furthermore, after the blood pressure measurement has ended, the CPU 18 carries out control so that the electromagnet portion 321 and the electromagnet portion 322 magnetically repel each other (ST75).

The magnetic polarity of the electromagnet portion 321 is reversed, for example.

Through this, the cuff 30 ceases to be secured, and the measurement subject can easily remove the cuff 30 after the blood pressure measurement as a result.

Figure 8:
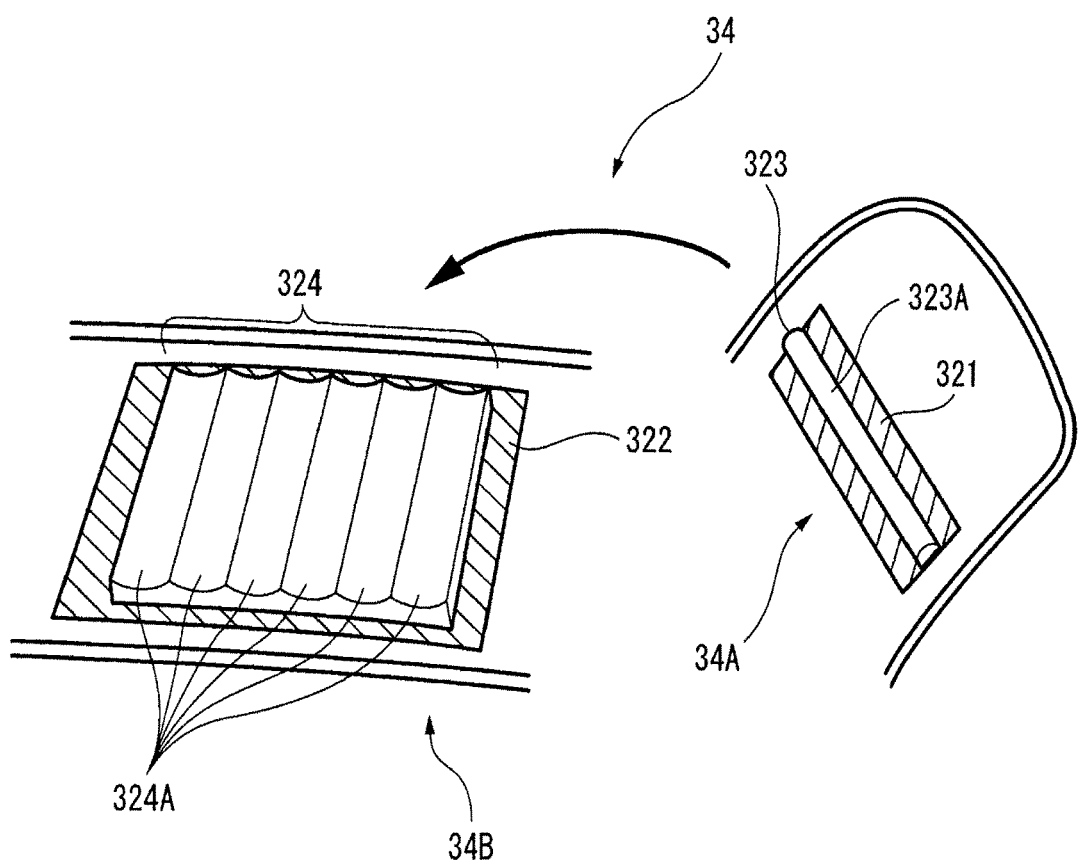
FIG. 8 is a diagram illustrating a securing portion in yet another example of the blood pressure measurement device illustrated in FIG. 1.

FIG. 8 is an external view illustrating the securing portion in yet another example of the blood pressure measurement device 1.

In the blood pressure measurement device shown in FIG. 8, a securing portion 34 is provided instead of the securing portion 32 of the blood pressure measurement device 1.

Note that in FIG. 8, constituent elements that are the same as those in FIG. 1 have been given the same reference numerals, and descriptions thereof will be omitted as appropriate.

The securing portion 34 includes an inner surface securing portion 34A and an outer surface securing portion 34B.

The inner surface securing portion 34A includes the electromagnet portion 321 and an engagement member 323 that is provided on the electromagnet portion 321 and that has a protruding portion 323A that extends in a direction that intersects (is orthogonal, in FIG. 8) to a wrapping state adjustment direction along which the wrapping state of the cuff 30 is adjusted.

The outer surface securing portion 34B, meanwhile, includes the electromagnet portion 322, and an engagement member 324 that is provided on the electromagnet portion 322 and that has a plurality of recessed portions 324A that engage with the protruding portion 323A of the engagement member 323.

Accordingly, the recessed portions 324A of the engagement member 324 extend in a direction approximately perpendicular to the wrapping state adjustment direction of the cuff 30. The plurality of recessed portions 324A are arranged along the wrapping state adjustment direction of the cuff 30.

The CPU 18 causes power to be supplied to the electromagnet portion 321 and the electromagnet portion 322 from the electromagnet drive circuit 23. Through this, the electromagnet portion 321 and the electromagnet portion 322 attract each other, the engagement member 323 and the engagement member 324 engage with each other, and the cuff 30 is secured.

Providing the engagement member 323 and the engagement member 324 in this manner makes it easy for the measurement subject to determine whether the cuff 30 has been secured; furthermore, if the measurement subject remembers where the engagement members engage, it is easy to reproduce the conditions under which the previous blood pressure measurement was carried out.

Although a plurality of the recessed portions 324A are provided here, a plurality of protruding portions 323A may be provided as well. When a plurality of protruding portions 323A are, provided, a single recessed portion 324A may be provided.

Furthermore, although the plurality of recessed portions 324A are connected to each other here, a predetermined interval may instead be provided therebetween.

Furthermore, although the securing portion 34 includes electromagnet portions in both the inner surface securing portion 34A and the outer surface securing portion 34B, the electromagnet portion may be provided in only one of the stated securing portions.

Figure 9:
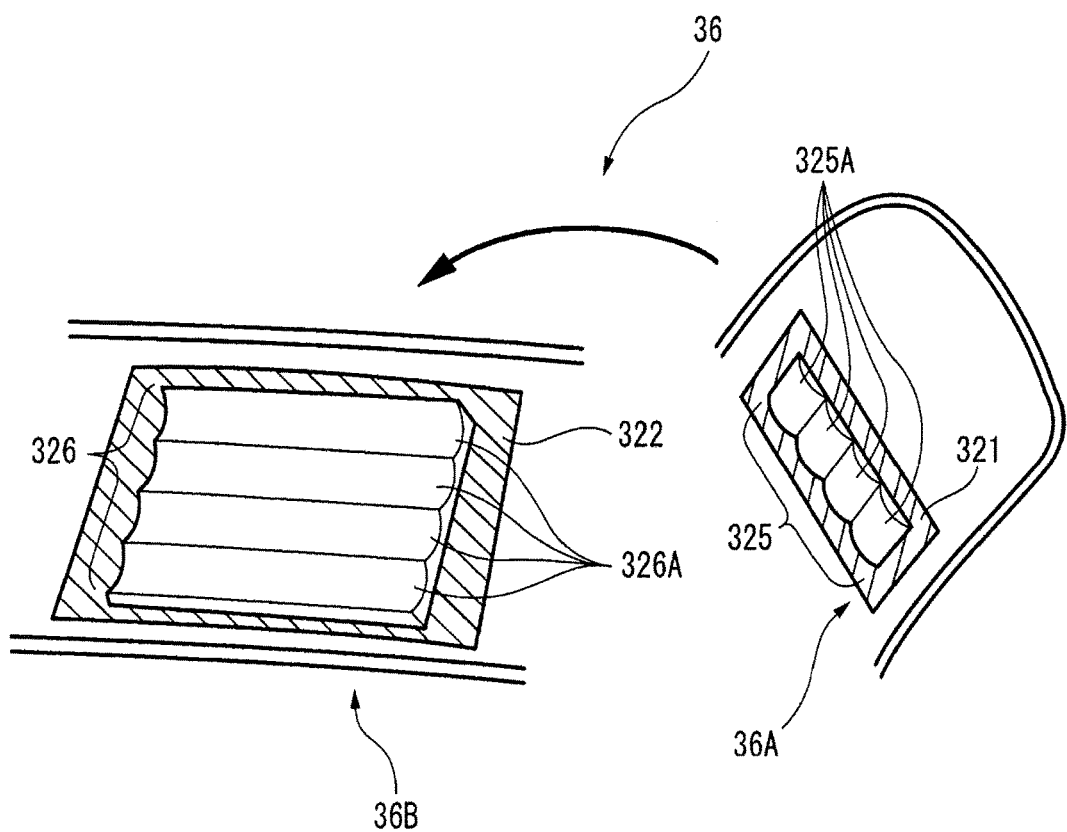
FIG. 9 is a diagram illustrating a securing portion in yet another example of the blood pressure measurement device illustrated in FIG. 1.

FIG. 9 is an external view illustrating the securing portion in yet another example of the blood pressure measurement device 1.

In the blood pressure measurement device shown in FIG. 9, a securing portion 36 is provided instead of the securing portion 32 of the blood pressure measurement device 1.

Note that in FIG. 9, constituent elements that are the same as those in FIG. 1 have been given the same reference numerals, and descriptions thereof will be omitted as appropriate.

The securing portion 36 includes an inner surface securing portion 36A and an outer surface securing portion 36B.

The inner surface securing portion 36A includes the electromagnet portion 321, and an engagement member 325 that is provided on the electromagnet portion 321 and that has a plurality of protruding portions 325A that extend in the wrapping state adjustment direction along which the wrapping state of the cuff 30 is adjusted.

The plurality of protruding portions 325A are arranged in a direction orthogonal to the wrapping state adjustment direction.

The outer surface securing portion 36B, meanwhile, includes the electromagnet portion 322, and an engagement member 326 that is provided on the electromagnet portion 322 and that has a plurality of recessed portions 326A that engage with the protruding portions 325A of the engagement member 325.

Accordingly, the recessed portions 326A of the engagement member 326 also extend in the wrapping state adjustment direction of the cuff 30, and the plurality of recessed portions 326A extend in a direction orthogonal to the wrapping state adjustment direction of the cuff 30.

The CPU 18 causes power to be supplied to the electromagnet portion 321 and the electromagnet portion 322 from the electromagnet drive circuit 23. Through this, the electromagnet portion 321 and the electromagnet portion 322 attract each other, the engagement member 325 and the engagement member 326 engage with each other, and the cuff 30 is secured.

Accordingly, the engagement member 325 can be adjusted by sliding relative to the engagement member 326 even in the case where the wrapping state is loose, which makes it easy to adjust how the cuff 30 is secured.

Figure 10:
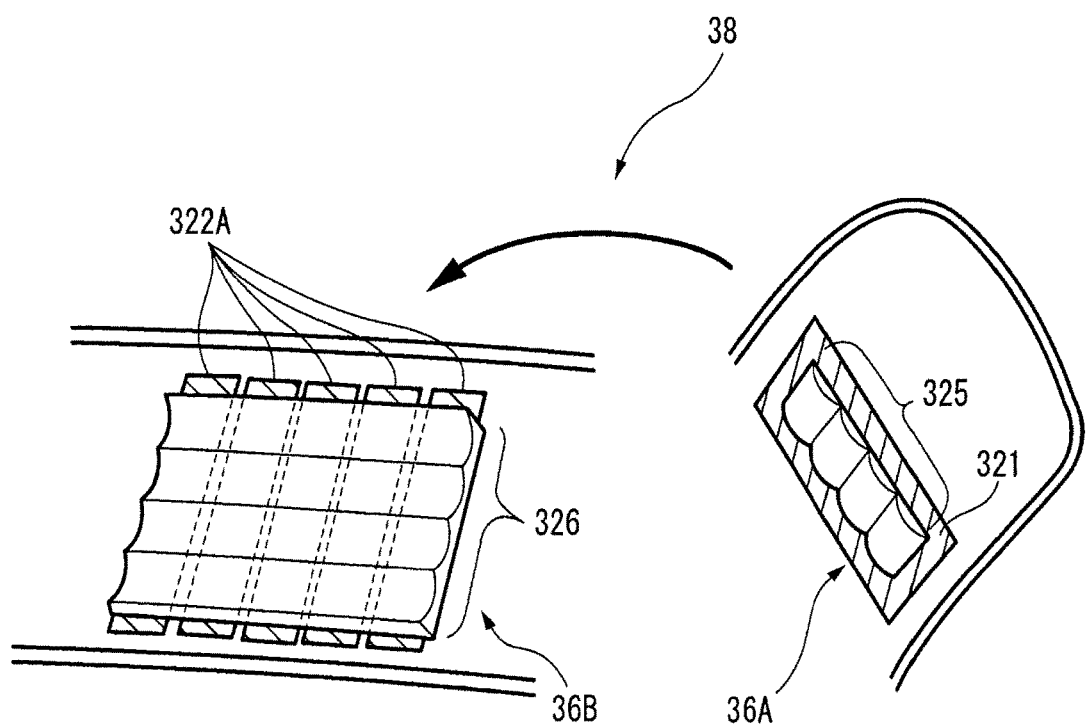
FIG. 10 is a diagram illustrating another example of the securing portion shown in FIG. 9.

FIG. 10 is a diagram illustrating another example of the securing portion shown in FIG. 9.

In the blood pressure measurement device shown in FIG. 10, a securing portion 38 is provided instead of the securing portion 36 of the blood pressure measurement device 1.

Note that in FIG. 10, constituent elements that are the same as those in FIG. 9 have been given the same reference numerals, and descriptions thereof will be omitted as appropriate.

The securing portion 38 differs from the securing portion 36 in that the electromagnet portion 322 is not configured of a single electromagnet portion, and is instead configured of a plurality of electromagnet portions 322A to which power is supplied individually from the electromagnet drive circuit 23.

Accordingly, the CPU 18 can carry out control so that power is supplied to the electromagnet portions 322A individually.

The plurality of electromagnet portions 322A are arranged along the wrapping state adjustment direction.

With respect to the cuff 30 being secured, the engagement member 325 is initially engaged with the engagement member 326 by supplying power to at least one of the plurality of electromagnet portions 322A.

Then, the CPU 18 stops the supply of power to the electromagnet portion 322A to which power had been supplied, and supplies power to the adjacent electromagnet portion 322A to which power had not been supplied.

For example, the CPU 18 changes the electromagnet portion 322A to which power is supplied in response to the passage of a predetermined amount of time.

Through this, the magnetic field emitted from the electromagnet portion 322 changes instantly, and as a result, the engagement member 325 slides upon the engagement member 326 while remaining engaged with the engagement member 326.

Accordingly, the strength of the wrapping state between the inner surface securing portion 36A and the outer surface securing portion 36B can be changed without manual input, and how the cuff is secured can be automatically adjusted.

The foregoing has described an embodiment in which the present invention is applied in a method that finds a blood pressure value from a cuff pressure detected while reducing a pressurizing pressure applied by the cuff 30; however, the present invention can be applied in the same manner in a method that finds a blood pressure value from a cuff pressure detected while increasing a pressurizing pressure applied by the cuff 30.

Note that the embodiment disclosed above is to be understood as being in all ways exemplary and in no way limiting. The scope of the present invention is defined not by the aforementioned descriptions but by the scope of the appended claims, and all changes that fall within the same essential spirit as the scope of the claims are intended to be included therein as well.

The present specification discloses the following items.

(1) A blood pressure measurement device includes a cuff that is used by being wrapped around a measurement area. The cuff includes a first securing portion, provided on one surface of the cuff, for securing the cuff to the measurement area in a wrapped state, and a second securing portion, provided on another surface of the cuff, for securing the cuff to the measurement area in a wrapped state. At least one of the first securing portion and the second securing portion includes an electromagnet portion. The blood pressure measurement device further includes a control unit that secures the cuff to the measurement area by controlling a magnetic force emitted from the electromagnet portion and causing the second securing portion to be attracted to the first securing portion.

(2) The blood pressure measurement device according to (1), in which the control unit increases the magnetic force emitted from the electromagnet portion in accordance with a pressurizing pressure applied by the cuff while the cuff is being inflated for blood pressure measurement.

(3) The blood pressure measurement device according to (1) or (2), in which the control unit reduces the magnetic force emitted from the electromagnet portion in accordance with a pressurizing pressure applied by the cuff while the cuff is being deflated for blood pressure measurement.

(4) The blood pressure measurement device according to any one of (1) to (3), further including a wrapping state determination unit that determines a wrapping state of the cuff on the measurement area based on a pressure in the cuff; here, the control unit controls the magnetic force emitted from the electromagnet portion in accordance with the wrapping state determined by the wrapping state determination unit.

(5) The blood pressure measurement device according to any one of (1) to (4), in which the control unit stops the supply of power to the electromagnet portion after the blood pressure measurement has ended.

(6) The blood pressure measurement device according to any one of (1) to (5), in which both the first securing portion and the second securing portion include the electromagnet portion, and the control unit carries out first control that controls the magnetic force so that the electromagnet portion of the first securing portion and the electromagnet portion of the second securing portion are attracted to each other by the magnetic force and second control that controls the magnetic force so that the electromagnet portion of the first securing portion and the electromagnet portion of the second securing portion repeal each other due to the magnetic force.

(7) The blood pressure measurement device according to (6), in which the control unit carries out the second control and releases the cuff from the measurement area after the blood pressure measurement has ended.

(8) The blood pressure measurement device according to any one of (1) to (7), in which the first securing portion further includes a first engagement member, and the second securing portion further includes a second engagement member that engages with the first engagement member.

(9) The blood pressure measurement device according to (8), in which the first engagement member is configured of a protruding member or a recessed member that extends in one direction, and the second engagement member is configured of a recessed member or a protruding member that engages with the protruding member or the recessed member of the first engagement member.

(10) The blood pressure measurement device according to (9), in which the one direction is a direction that intersects with a wrapping state adjustment direction in which a wrapping state of the cuff is adjusted, and a plurality of the protruding member or the recessed member of the first engagement member are provided so as to be arranged along the wrapping state adjustment direction.

(11) The blood pressure measurement device according to (9), wherein the one direction is a wrapping state adjustment direction in which a wrapping state of the cuff is adjusted.

(12) The blood pressure measurement device according to (11), wherein the protruding member or the recessed member is provided on the electromagnet portion; and the electromagnet portion is configured of a plurality of electromagnet portions that are arranged along the one direction and are capable of being controlled individually by the control unit.

INDUSTRIAL APPLICABILITY

According to the present invention, a novel blood pressure measurement device that does not employ a surface fastener to secure a cuff can be provided.

While the present invention has been described in detail with reference to a specific embodiment, it will be clear to one of ordinary skill in the art that many variations and modifications can be made without departing from the essential spirit and scope of the present invention.

This application claims the benefit of Japanese Patent Application No. 2012-061929, filed Mar. 19, 2012, which is hereby incorporated by reference herein in its entirety.

REFERENCE SIGNS LIST 1 blood pressure measurement device
10 main body unit
11 pressure sensor
12 pump
13 valve
14 oscillation circuit
15 pump drive circuit
16 valve drive circuit
17 power source
19 display unit
21 operating unit
21A power switch
21E measure/stop switch
22 memory
23 electromagnet drive circuit
30 cuff
31 air bladder
32 securing portion
32A inner surface securing portion
32B outer surface securing portion

The invention claimed is:

1. A blood pressure measurement device comprising:
a cuff that is wrapped around a measurement area, the cuff including: (i) a first securing portion provided on a first surface of the cuff, the first securing surface being configured to secure the cuff to the measurement area in a wrapped state, and (ii) a second securing portion provided on a second surface of the cuff, the second securing portion being configured to secure the cuff to the measurement area in the wrapped state, at least one of the first securing portion and the second securing portion including an electromagnet portion; and a processor programmed to:
secure the cuff to the measurement area by driving the electromagnet portion causing the second securing portion to be electromagnetically attracted to the first securing portion;
control a magnetic force emitted by the electromagnet portion in accordance with a pressurizing pressure applied by the cuff; and
increase the magnetic force provided from the electromagnet portion in accordance with the increased pressure applied by the cuff in response to the cuff being inflated for blood pressure measurement.

2. The blood pressure measurement device according to claim 1, wherein the processor is programmed to reduce the magnetic force emitted from the electromagnet portion in accordance with the pressurizing pressure applied by the cuff while the cuff is being deflated for blood pressure measurement.

3. The blood pressure measurement device according to claim 1, wherein the processor is programmed to:
determine a wrapping state of the cuff on the measurement area based on a pressure in the cuff; and
control the magnetic force emitted from the electromagnet portion in accordance with the determined wrapping state.

4. The blood pressure measurement device according to claim 1, wherein the processor is programmed to stop supply of power to the electromagnet portion after the blood pressure measurement has ended.

5. The blood pressure measurement device according to claim 1, wherein:
the first securing portion includes the electromagnet portion, and the second securing portion includes a second electromagnet portion; and
the processor is programmed to perform (i) a first control that controls the magnetic force so that the electromagnet portion of the first securing portion and the second electromagnet portion of the second securing portion are electromagnetically attracted to each other by the magnetic force, and (ii) a second control that controls the magnetic force so that the electromagnet portion of the first securing portion and the second electromagnet portion of the second securing portion repel each other due to the magnetic force.

6. The blood pressure measurement device according to claim 5, wherein the processor is programmed to perform the second control and release the cuff from the measurement area after the blood pressure measurement has ended.

7. The blood pressure measurement device according to claim 1, wherein:
the first securing portion further includes a first engagement member; and
the second securing portion further includes a second engagement member that engages with the first engagement member, wherein:
the first engagement member includes a protruding member or a recessed member that extends in one direction; and
the second engagement member includes a recessed member or a protruding member that engages with the protruding member or the recessed member of the first engagement member.

8. The blood pressure measurement device according to claim 7, wherein:
the one direction is a direction that intersects with a wrapping state adjustment direction in which a wrapping state of the cuff is adjusted; and
a plurality of the protruding member or the recessed member of the first engagement member are provided so as to be arranged along the wrapping state adjustment direction.

9. The blood pressure measurement device according to claim 7,
wherein the one direction is a wrapping state adjustment direction in which a wrapping state of the cuff is adjusted.

10. The blood pressure measurement device according to claim 9, wherein:
the protruding member or the recessed member is provided on the electromagnet portion; and
the electromagnet portion includes a plurality of electromagnet portions that are arranged along the one direction, the plurality of electromagnet portions are configured to be controlled individually by the processor.

11. The blood pressure measurement device according to claim 1, wherein
increasing the magnetic force provided from the electromagnet portion causes the first securing portion to be more strongly secured to the second securing portion when the pressure applied by the cuff is increased.

12. A blood pressure measurement device comprising:
a cuff that is wrapped around a measurement area, the cuff including: (i) a first electromagnet provided on a first surface of the cuff, the first electromagnet being configured to secure the cuff to the measurement area in a wrapped state, and (ii) a second electromagnet provided on a second surface of the cuff, the second electromagnet being configured to secure the cuff to the measurement area in the wrapped state; and
a processor programmed to:
secure the cuff to the measurement area by driving one of the first or second electromagnets such that the second electromagnet is electromagnetically attracted to the first electromagnet;
control a magnetic force emitted by the one of the first or second electromagnets in accordance with a pressurizing pressure applied by the cuff; and
increase the magnetic force provided from the one of the first or second electromagnets in accordance with the increased pressure applied by the cuff in response to the cuff being inflated for blood pressure measurement.

13. The blood pressure measurement device according to claim 12, wherein:
the first electromagnet further includes a first recess or protrusion; and
the second electromagnet further includes a second recess or protrusion that engages with the first recess or protrusion.

* * * * *